United States Patent
Carson

[19]

[11] Patent Number: 5,931,862
[45] Date of Patent: Aug. 3, 1999

[54] MEDICAL LEAD AND METHOD OF MAKING AND USING WITH SODIUM SULFOSUCCINIC ESTER

[75] Inventor: Dean F. Carson, Mountain View, Calif.

[73] Assignee: Pacesetter, Inc., Sunnyvale, Calif.

[21] Appl. No.: 08/995,685

[22] Filed: Dec. 22, 1997

[51] Int. Cl.⁶ .............................. A61N 1/05; A61N 1/04
[52] U.S. Cl. ........................ 607/120; 607/119; 607/116
[58] Field of Search ................................ 607/116, 119, 607/120

[56] References Cited

U.S. PATENT DOCUMENTS

| | | |
|---|---|---|
| 3,632,387 | 1/1972 | Sutherland . |
| 4,442,841 | 4/1984 | Uehara et al. . |
| 4,557,957 | 12/1985 | Manniso . |
| 4,743,480 | 5/1988 | Campbell et al. . |
| 4,752,617 | 6/1988 | Kern ........................................ 514/547 |
| 4,840,186 | 6/1989 | Lekholm et al. . |
| 4,911,713 | 3/1990 | Sauvage et al. . |
| 4,972,846 | 11/1990 | Owens et al. . |
| 5,090,422 | 2/1992 | Dahl et al. . |
| 5,120,833 | 6/1992 | Kaplan . |
| 5,269,810 | 12/1993 | Hull et al. . |
| 5,330,520 | 7/1994 | Maddison et al. . |
| 5,358,516 | 10/1994 | Myers et al. . |
| 5,439,485 | 8/1995 | Mar et al. . |
| 5,466,252 | 11/1995 | Soukup et al. . |
| 5,483,022 | 1/1996 | Mar . |
| 5,609,622 | 3/1997 | Soukup et al. . |

FOREIGN PATENT DOCUMENTS 3305271  8/1984  Germany .

OTHER PUBLICATIONS

Caryl, "Sulfosuccinic Esters," Industrial and Engineering Chemistry, vol. 33, No. 6, Jun. 1941, pp. 731–737.

Patent Application Serial No. 08/663,850, Attorney Docket VT0215–US1, filed Jun. 14, 1996.

*Primary Examiner*—William E. Kamm
*Assistant Examiner*—Carl H. Layno
*Attorney, Agent, or Firm*—Steven M. Mitchell

[57] ABSTRACT

A continuous sheath of open-celled porous plastic, preferably ePTFE, is used on the outside of a medical lead, extending along the lead body and the electrodes. Because the plastic is open-celled, when the pores are filled with saline, the lead can deliver electrical energy through the pores in the plastic. Pore size is chosen to discourage tissue ingrowth while allowing for defibrillation energy delivery and electrical signals through it. The porous plastic has a biocompatible wetting agent applied to it to speed the process of filling the pores with saline.

19 Claims, 4 Drawing Sheets

MEDICAL LEAD AND METHOD OF MAKING AND USING WITH SODIUM SULFOSUCCINIC ESTER

FIELD OF THE INVENTION

The present invention relates generally to medical leads for sensing signals from and delivering electrical energy to body tissues. This invention especially relates to leads having a porous covering over their electrodes that must be wet out prior to use, and a method for wetting out the porous covering.

BACKGROUND OF THE INVENTION

A medical lead as referred to herein is an at least partially insulated electrical conductor that interfaces with a patient's body tissue at one end and with a detector and/or energy source at the other. A medical lead may have a covering of an open-celled porous membrane material such as expanded polytetrafluoroethylene (ePTFE). Some prior art examples of such leads are given in the following paragraphs. Where these membranes cover the electrodes of such leads, the pores of the membranes must be filled with conductive fluid such as saline or blood or other bodily fluids to conduct current through them. To facilitate filling of the pores by bodily fluids or saline, a wet-out agent may be applied to the membrane. Without such a wet-out agent, several days may be required for infusion of the pores by bodily fluids. This would delay the electrical testing of the implanted lead, requiring the patient to return for testing at a later date, and rendering the lead nonfunctional until then. On the other hand, faster wet-out time allows shorter implant time, which provides a reduced risk of infection, bleeding, and tissue dehydration. It is desired that the electrical conductivity not be altered significantly over time; that is, the impedance of the electrode system at implant should be similar to that chronically. Selection and application of a wet-out agent that can almost immediately and completely wet out ePTFE is the subject of this invention.

As used herein, the term "defibrillation" refers to either or both atrial and ventricular defibrillation.

In U.S. Pat. No. 5,090,422 to Dahl et al., which is incorporated herein by reference, a porous coating or sheath is used on an endocardial defibrillation lead to create a dissection plane with respect to adjacent tissue, to substantially prevent tissue ingrowth. Materials listed for this application include porous polyurethane and porous polytetrafluoroethylene (PTFE) used with a wetting agent or surface-modified. However, there is no disclosure of any specific wet-out agent, nor of means for its application or for modifying the surface.

In U.S. Pat. No. 5,358,516 to Myers et al., a lead assembly is disclosed having an insulated conductor covered by an ePTFE sheath. Because the ePTFE sheath is used over only the insulated conductor, but not the electrode, no means is necessary to facilitate wetting out by bodily fluids.

In U.S. Pat. No. 5,330,520 to Maddison et al., which is incorporated herein by reference, at least a portion of the outer conductor is surrounded by an outer conductive sheath formed from a suitable material having a nonabrasive effect. To insulate portions of the lead in the nonelectrode regions, pores in the conductive porous sheath are filled with a nonconductive polymer. The outer conductive sheath may be a porous polymeric sheath whose pores are infused by a conductive substance such as body fluids, a conductive gel, or a layer of poly (2-hyroxyethylmethacrylate) (polyHEMA) or Nafion® perfluorosulphonic acid. No means is disclosed for facilitating, accelerating, or enhancing wetting out of the pores by bodily fluids. According to the patent, "one particular advantage of the lead" is that "fibrous ingrowth may occur in the porous portion of the lead, thus securing the lead to the heart wall", implying that a pore size that promotes tissue ingrowth is preferred. However, this would make lead extraction difficult and is not a desirable feature for long term implantable leads.

The only method to wet out the ePTFE membrane prior to implant currently found in the literature is to briefly immerse it in an alcohol solution and then slowly extract the alcohol in a saline solution. A time-consuming step, this "alcohol approach" method is described in both Gelman and Millipore product catalogs for filtration membranes and has been successfully used in acute canine animal studies using ePTFE-covered defibrillation lead electrodes.

In the field of vascular grafts, some grafts are impregnated with gelatin or collagen (U.S. Pat. No. 5,120,833) to prevent blood leakage through them. Woven polyester (Dacron®) vascular grafts have inherently excessive porosity that requires either preclotting with the patient's own blood or preloading with a crosslinked gelatin or collagen by the manufacturer. Knitted Dacron grafts and ePTFE grafts have lower porosity that do not require preclotting steps. Because of the relatively large pore size of woven Dacron grafts compared to ePTFE, perfusion impregnation processes are simple and do not require high pressures to force liquids through the graft walls (U.S. Pat. Nos. 4,911,713 and 5,120,833). The perfusion process always includes crosslinking steps that control its dissolution rate, typically with the gelatin-loaded grafts such as Gelseal®, the gelatin is claimed to completely hydrolyze in 14 days. Grafts need the gelatin in place for two weeks to allow for external tissue growth into the outer surface and, more importantly, to allow for the surface of the lumen to become completely clotted by the patient's own blood to minimize bleeding.

SUMMARY OF THE INVENTION

In the present invention, a continuous sheath of open-celled porous plastic, preferably ePTFE, is used on the outside of the defibrillation lead, extending along the lead body and the electrodes, in such a way that the lead is isodiametric along its length, and is very strong in tension as is required for lead removal. Because the plastic is an open-cell porous structure, when the pores are filled with conductive fluid the lead can deliver defibrillation energy through the pores in the plastic. Pore size is chosen to discourage tissue ingrowth. The nonelectrode portions of the lead are insulated with silicone rubber, polyurethane, non-porous fluoropolymer, or the like, beneath the porous sheath. The ePTFE sheath is treated to accelerate the normally slow occurring wet-out process. The materials and methods used to treat the ePTFE are disclosed.

The present application includes a method to modify a hydrophobic porous ePTFE membrane such that it becomes electrically conductive after insertion into the human body. The membrane can be in the form of a tube to insulate an implantable pacing or defibrillation lead or sheet for a patch electrode such that after insertion into the blood stream or subcutaneous pocket it quickly wets out (the pores fill with bodily fluids). A quick wet out allows for device electrical testing to be done using electrodes that reside under the ePTFE insulation and closure of implantation incisions to be made as soon as possible. Specifically, a means to render the membrane electrically conductive in a relatively short time period by impregnating the membrane with a biocompatible wet-out agent is disclosed.

In a first embodiment, the primary agent is a surfactant that is applied by simple, noncontact methods such as spraying or dipping, or by more controlled, contact methods such as brushing.

In a second embodiment, the primary agent is gelatin, another protein (e.g., collagen, albumin) or another similar material (e.g., agar). The impregnation of the ePTFE may be achieved via immersion/vacuum, perfusion, or pressure processes. As a wet-out agent for implantable electrodes, the gelatin does not require crosslinking and can dissolve away immediately. After the gelatin accomplishes its function to wet out the ePTFE, it may be allowed to be washed away from the surface as it dissolves into the blood.

It is therefore an object of the present invention to provide a means for facilitating wet out of a porous membrane covering medical lead electrodes.

It is a further object of the present invention to provide a method for applying a wetting agent to a porous membrane covering medical lead electrodes.

It is a further object of the present invention to provide a wetting agent that is sterilizable using ethylene oxide (ETO) without affecting wet-out efficacy.

It is a further object of the present invention to provide a wetting agent that reduces wet out time to less than 30 seconds.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE DRAWINGS

Figure 1:
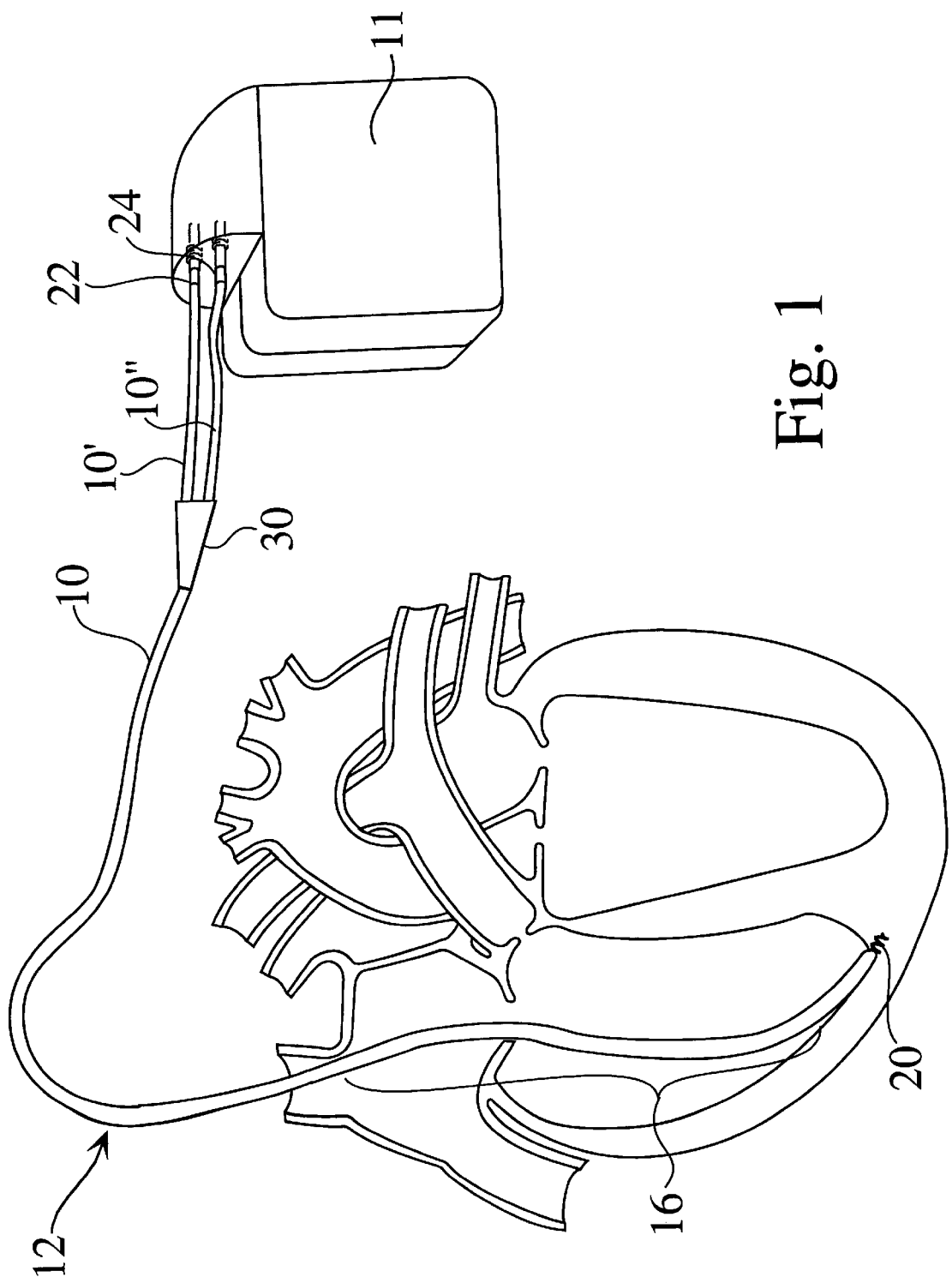
FIG. 1 shows a lead of the present invention having a continuous porous tubular covering on the electrodes and lead body, implanted within the heart.

FIG. 1 shows a lead 12 of the present invention having a continuous porous tubular covering 10 on the electrodes and lead body, implanted within the heart. Additional porous tubular coverings 10', 10" are located on the body of each connector branch 22, 24, each of which is electrically and mechanically coupled to pulse generator 11. Pulse generator 11 has an electrically active housing for use as an electrode. Alternatively or additionally, a superior vena cava (SVC) lead, epicardial lead, or other subcutaneous lead may be used. This lead is further described in copending U.S. patent application Ser. No. 08/663,850, filed on Jun. 14, 1996 now U.S. Pat. No. 5,755,762, which is assigned to the assignee of the present application and is incorporated herein by reference.

Figure 2:
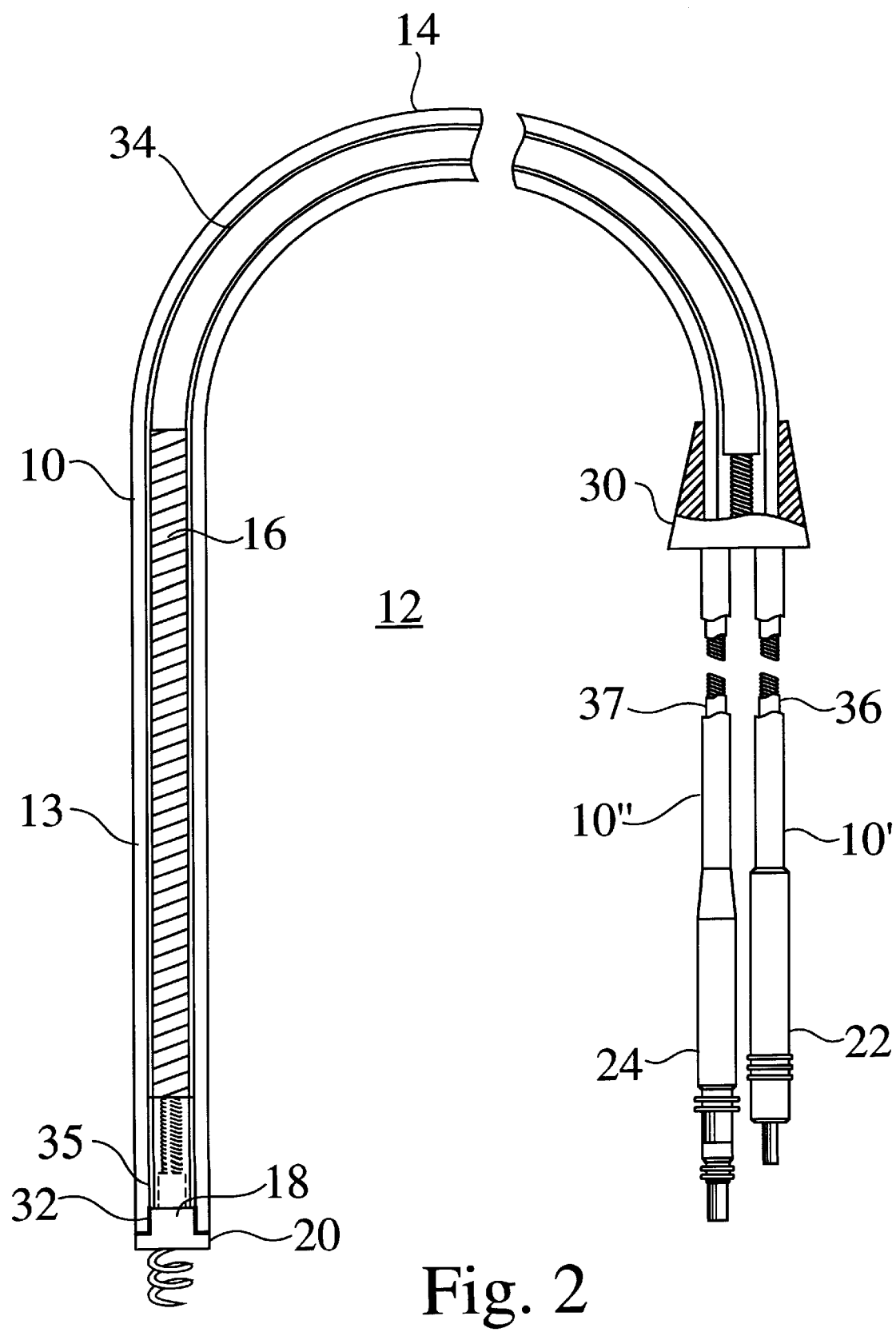
FIG. 2 is a partial cut away view of the lead of FIG. 1.

FIG. 2 is a partial cut away view of lead 12 of FIG. 1. A continuous sheath of open-celled porous plastic, preferably ePTFE, is used as a porous tubular covering 10 on the outside of a defibrillation lead 12. Covering 10 extends along a lead body 14, an electrode 16 and a shank 18 of a distal pacing electrode 20. Lead 12 is isodiametric along its length, and is very strong in tension as is required for lead removal. Because the plastic is open-celled, when the pores are filled with saline or body fluid, lead 12 can deliver defibrillation energy from underlying electrode 16 through the pores in the plastic to the cardiac tissue. Pore size is chosen small enough to discourage tissue ingrowth, but large enough that current can be delivered through covering 10 when its pores are filled with fluid. Underlying electrode 16 may be of any defibrillation or pacing electrode construction known in the art, such as platinum iridium coil, braided carbon fibers, wound titanium ribbon, titanium nitride or platinum black coated rings, or coiled platinum iridium coils as described in U.S. Pat. No. 5,439,485 to Mar et al. and assigned to the assignee of the present invention and incorporated herein by reference.

Alternatively, underlying electrode 16, as well as lead body 14, may be of other constructions that would otherwise be unsuitable were it not for covering 10. For example, electrode 16 and/or lead body 14 may be more mechanically fragile (e.g., utilizing fragile coatings such as platinum black, possessing lower tensile strength, being less fatigue resistant, being less abrasion resistant than currently-used extruded 50A silicone rubber which is considered to have the lowest accepted abrasion resistance for lead body materials), less biocompatible from a mechanical design point of view (due to rougher edges, more invaginations, crevices, or places where tissue attachments would otherwise form, etc.), or more complex in overall shape (which would normally be difficult to explant).

In conventional leads, the length of the right ventricular (RV) defibrillation electrode 16 is limited by the length of the RV chamber because of danger of trauma to the tricuspid valve. Because of the nonfibrosing nature of lead 12, and its isodiametricity, the defibrillation electrode can be made longer than in conventional leads because trauma to the tricuspid valve and potential ingrowth into it is drastically reduced.

Portions of lead 12 not covered by porous tubular covering 10 are lead connectors 22, 24, distal pacing electrode 20, and a joint 30 of connectors 22, 24 to lead body 14. Critical portions of lead 12 that are covered are the regions located within the vein and cardiac chambers, with enough of covering 10 extending from the venous entry site to be grasped for lead removal. Ideally, covering 10 extends proximally all the way to the connector or the furcation 30 of connectors if there is more than one connector as in FIGS. 1 and 2.

Distally, covering 10 extends over the shank 18 of the distal pacing electrode 20 and attaches to it, using an adhesive 32 and/or a mechanically crimped sleeve. In addition to bonding covering 10 to shank 18, adhesive 32 also electrically insulates shank 18 from the cardiac tissue, which is important for decreasing surface area to increase current density for pacing.

The conductors in lead 12 which electrically and mechanically couple electrodes 16 and 18 to connectors 22 and 24 may be of any structure or combination of structures known in the art, such as coaxial coils separated by an insulating tube, side-by-side cables or coils insulated with a fluoropolymer, silicone, polyimide, or polyurethane, coiled drawn filled tube (DFT, Fort Wayne Metals, Ft. Wayne, Ind.) cables according to U.S. Pat. No. 5,483,022 to Mar, which is assigned to the assignee of the present invention and incorporated herein by reference, or a multipole helix of Lekholm et al. as described in U.S. Pat. No. 4,840,186 and incorporated herein by reference. Preferably, the nonelectrode portions of lead 12 are electrically insulated with an insulator 34, 35, 36, 37, which may be silicone rubber, polyurethane, or nonporous fluoropolymer tubing located between coaxial coiled conductors and beneath porous tubular covering 10, as described in U.S. Pat. No. 5,358,516 to Myers et al. Alternatively, multiple conductors may lie side by side, and may be individually insulated with a fluoropolymer coating, silicone tubing, or the like. As another alternative, the pores of porous tubular covering 10 may be filled with an insulating material in the nonelectrode portions of the lead; however, care must be taken in material choice to ensure that the structure is not altered from a nonfibrosing structure to one that produces fibrous tissue ingrowth.

Porous tubular covering 10 may be made of a fluoropolymer, polyester, polyurethane, cellulose acetate, mixed esters of cellulose, acrylic copolymer on nylon support, polyvinyl difluoride, polysulfone, polypropylene, cellulose nitrate, polycarbonate, nylon, and polyethylene. Preferably, the covering material is a fluoropolymer such as PTFE, fluorinated ethylene propylene (FEP), or perfluoroalkoxyvinyl ether (PFA), and most preferably, PTFE. Covering 10 may be a composite of two or more materials, such as a laminate of acrylic copolymer on a nylon support. The structure of tubular covering 10 is preferably expanded, such as expanded polytetrafluoroethylene, but may alternatively be woven, felt, fused mesh, or the like.

The structure of the outer surface of porous tubular covering 10 is preferably chosen to reduce fibrous ingrowth. However, the inner layers of tubular covering 10 may have larger pores, which would allow more saline within the material, thereby increasing conductivity, as would be desirable in regions covering electrode 16. Overall, the material is characterized by pore sizes suitable to allow penetration of bodily fluids but small enough such that a dissection plane or interface surface is formed so that tissue ingrowth is properly controlled upon chronic placement in the body. The pores over nonelectrode regions may be filled with a nonconductive or conductive polymer to further prevent tissue ingrowth. Likewise, the conductive portions may have pores filled with a conductive polymer to further prevent tissue ingrowth, such as a hydrogel, for example, polyethylene oxide (PEO).

Lead 12 is supplied with a wet-out agent 13 such as a surfactant, hydrogel, gelatin, or a combination of these, applied so that the lead automatically wets out almost immediately upon contact with body fluids. Surfactants of the sulfosuccinic ester class may be especially suitable for this application. Two surfactants successfully tested by the inventor include sodium dioctyl sulfosuccinate (also known as docusate sodium, or DSS) and tridodecylmethylammonium chloride (TDMAC). DSS is preferably applied from a 1–10% DSS in isopropanol (IPA) solution, and most preferably 2%, and TDMAC is preferably applied from a 10–20% TDMAC in IPA solution, and most preferably 10%. The lead may be implanted dry as packaged to be wet out directly in blood, or may be placed in sterile saline to be wet out prior to insertion into the patient.

Figure 3:
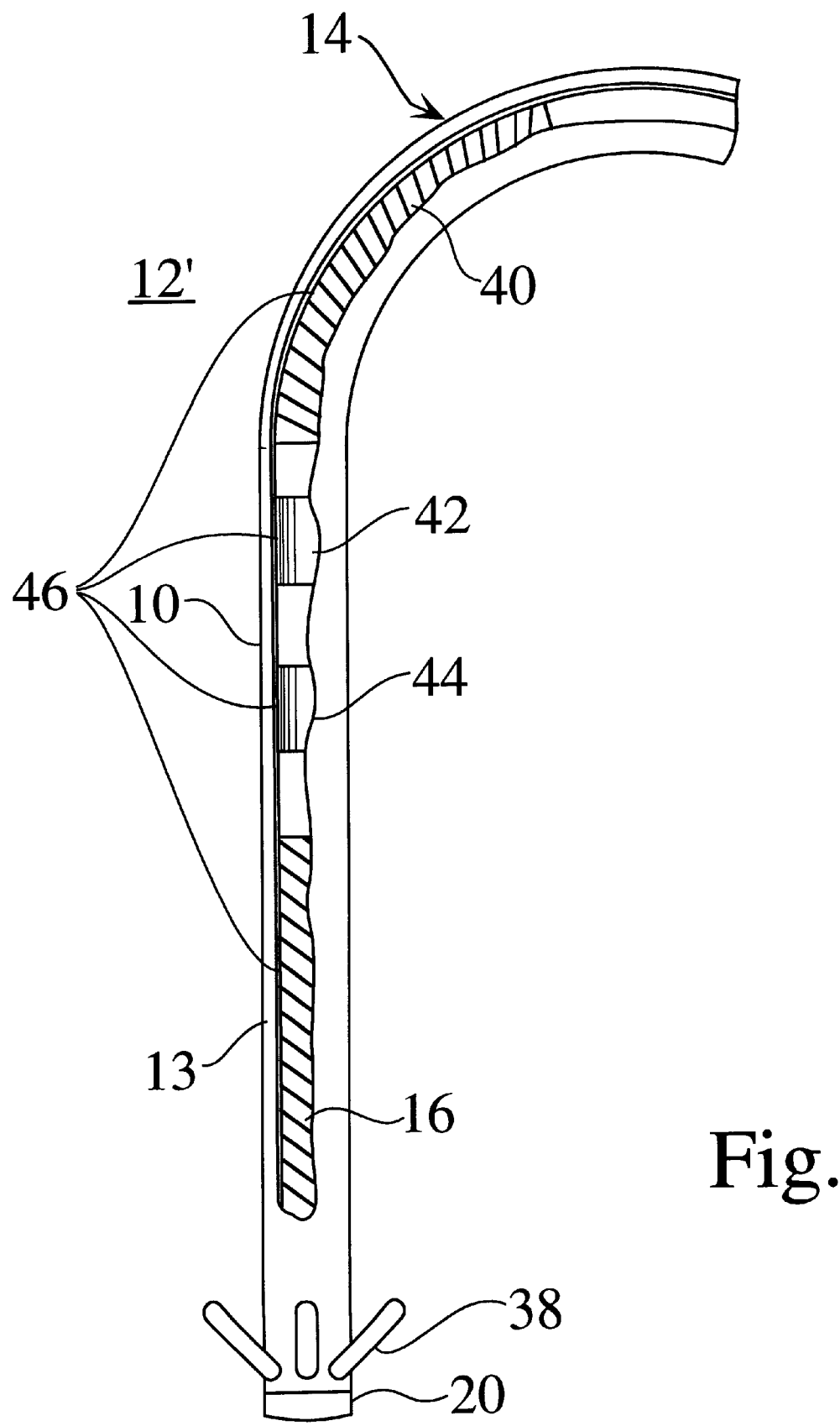
FIG. 3 is a partial cut away view of an alternative embodiment of the lead of the present invention.

FIG. 3 is a partial cut away view of an alternative embodiment of the lead of the present invention. Lead 12' has tines 38, for anchoring the distal end of the lead into the trabeculae of the patient's heart. In addition to distal pacing electrode 20 and RV defibrillation electrode 16, lead 12' has SVC electrode 40, and two atrial pacing/sensing electrodes 42 and 44. Porous tubular covering 10 extends over lead body 14, electrodes 40, 42, 44, and 16, down to the shank of distal pacing electrode 20. Except for tines 38, the lead is isodiametric from lead body 14 all the way to the distal end of the lead.

Because continuous contact between the inner diameter of ePTFE covering 10 and sensing rings 42, 44 or defibrillation electrode coils 16, 40 may be crucial to their performance, a thin layer of hydrogel 46 between ePTFE 10 and the electrodes may be used. The hydrogel should be chosen to have a relatively fast rate of hydration to become conductive as soon as possible. The thickness and maximum volume swell should be balanced so that unnecessary stress is not placed on the lead. Also, the outer diameter of the lead should not be increased due to hydrogel swelling underneath.

Hydrogel volume swell may be tailored by varying the molecular weight and/or crosslinking to optimize the design. Hydrogel selection may not be limited to just those with current blood-contacting biocompatibility since this may be considered a noncontacting application. Polyvinyl alcohol (PVA), poly (n-vinyl pyrrolidone) (PVP), PEO, polyacrylamide, polymethacrylic acid, and PHEMA may be suitable for this application. The nonsoluble hydrogel would permanently and physically occupy the space and ensure no interruptions in sensing.

The sensing rings may be porous in which case the hydrogel may be coated onto it using a solvent. Thermally attaching a hydrogel coating (i.e., melting it on) may be an alternate process, but because of the fragile nature of the porous coatings, especially sintered bead types, they may not withstand the pressures generated. Many hydrogels do not flow upon heating and their melt viscosities are very high. The electrode pores may be used to provide a mechanical anchor for the hydrogel. Alternatively or additionally, chemical bonding (covalently or otherwise) of the hydrogel to the metal may be employed.

Figure 4:
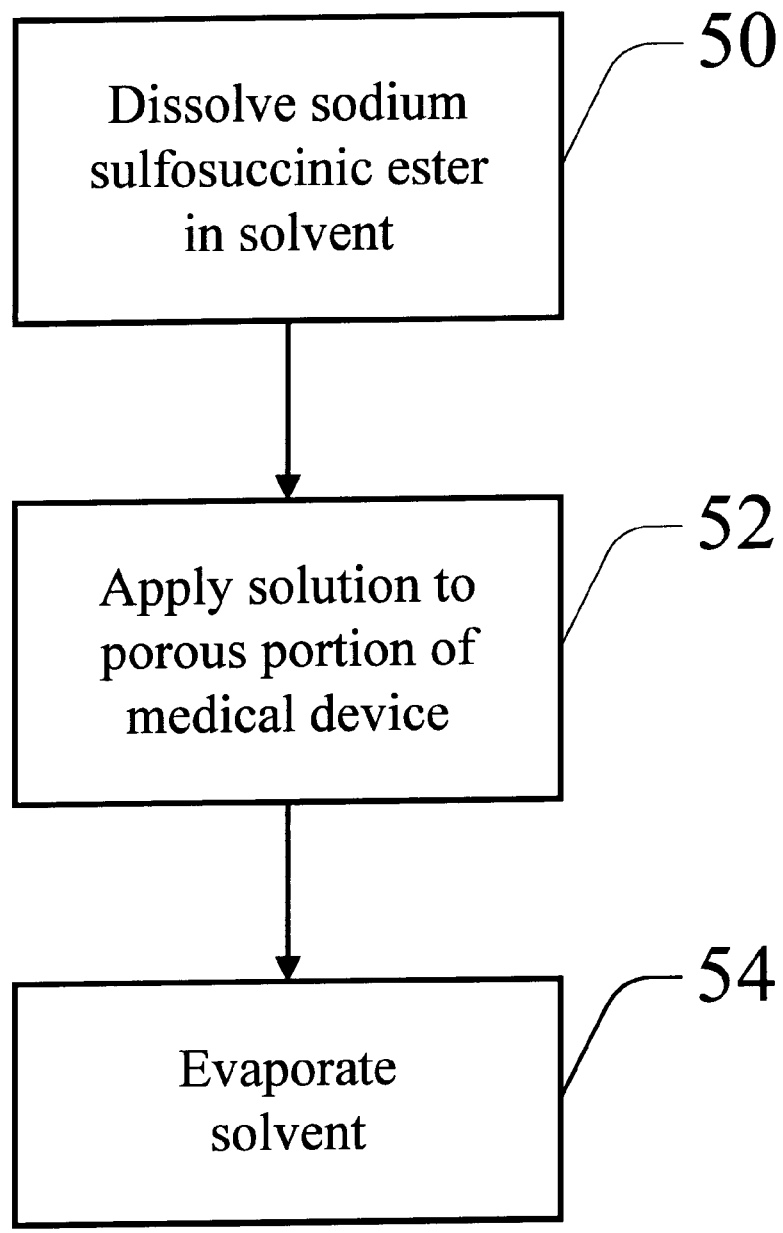
FIG. 4 is a flowchart showing the steps of the invention.

FIG. 4 shows a method for applying a wetting agent to a porous portion of a medical device. In step 50, a sodium sulfosuccinic ester is dissolved in a solvent to form a sodium sulfosuccinic ester solution. In step 52, the resulting sodium sulfosuccinic ester solution is applied to a portion of the porous portion of the medical device. In step 54, the solvent is evaporated off.

Simple Wetting Agent Application: Non-Contact Methods

Simple noncontacting methods, including dipping, and spraying, may be used to apply the solution to the lead without contacting the ePTFE. These methods may not allow accurate control of the amount applied since, for example, only a fraction of solution sprayed at a lead would actually hit the lead. However, the process may be validated to be in control by using extraction methods to show that consistent amounts of wet-out agent were being applied. The entire lead may be treated with the wetting agent; alternatively, by masking the nonelectrode regions, only the electrode regions may be treated. If the wetting agent is a surfactant, preventing the sealing o-rings and pins from being coated is recommended.

The ePTFE tubing can be pretreated with wet-out agents such as DSS either before or after the tubing is installed over the lead body. Precoating the ePTFE tubing or specific sections prior to putting it over the lead would prevent scrapping the entire lead if the coating process were not 100% successful. The wetting agent may be applied by simply dipping the tubing or lead into a solution containing DSS. In fact, of the wetting agents and application methods tested, the inventor has found that the most effective wet-out agent is DSS, applied from a 2% DSS in isopropyl alcohol (IPA) solution, using simple dipping and drying techniques under normal ambient conditions. Alternatively, other solvents and other alcohols may be used to apply the DSS.

Also, while 2% is the most preferred concentration, 1–10% would be suitable, with 1–5% preferred. An alternative to air drying under ambient conditions is to use heat and/or vacuum to help dry the lead. The article should be kept horizontal during or at least after dipping to prevent gravitational pooling effects at one end. Rotation may also keep the solution uniformly applied during drying. The article should be kept straight during dipping to prevent changing the porosity and hence solution uptake. The pores may temporarily collapse during bending or arcing which would make the internal volume change and hence loading level.

The time for the loading solution to fill all of the pores is very short and almost immediate, as seen by the change of color of the tubing. Upon wetting out, by either the loading solution or by saline after it is loaded, ePTFE turns from an opaque white to a translucent gray color. The ability to see fine details through the tubing is possible (such as defibrillation electrodes) if the wall is thin (e.g., 0.10 inches or less).

Visual microscopic examination shows no air bubbles are trapped in the pores when pretreated tubing is immersed into saline. This indicates that the conductive pathway is completely formed and at its maximum almost immediately. Because the pores are only coated by a solution with only about 2% solids, the DSS does not occupy any significant volume in the pores. This allows for the pores to fill primarily with bodily fluids, which will possess the proper electrolytes and thus ionic concentration for a stable conductivity over time, since about 55% of blood is fluid (plasma), of which about 90% is water.

Controlled-Quantity Wetting Agent Application: Contact Methods

Contacting methods may be used to apply wetting out agent to specific locations along lead. The following types of applicators may be used while rotating the lead and moving an applicator linearly, or with the applicator fixed and the lead moving, or with the lead fixed and only the applicator moving. In each case, solution is delivered through tubing that is connected to one or several of the following ePTFE contacting applicators:

1. Solid tip applicator. Solution is applied with tip that has no moving parts (e.g., bristles).
2. Flexible tip. Some part(s) of the applicator brush are flexible, preferably the contact portion, to conform to the lead and to evenly spread solution over the surface. Flexible tips may includes flexible films fashioned in a brush shape or used as an iris diaphragm to coat the entire outer diameter of a lead as it is pulled through. Any elastomeric material such as silicone or polyurethane may be employed.
3. Flexible brush. This is similar to a paintbrush, having flexible bristles or strands of natural or synthetic material that wick the solution to the tip and apply it uniformly to the surface of the lead or tubing.
4. Foam/Swab brush. This is similar to paintbrush but uses any type and shape of open- or closed-cell, synthetic (polymers such as polyester or urethane) or natural foam, or woven or nonwoven natural or synthetic swabs. It includes natural (such as cotton, abaca, or cellulose) or synthetic (such as polyester, urethane, polypropylene, nylon, or composites of thereof) fabrics employed in the manufacture of wipes.

A controlled-quantity application method using a solid tip applicator was tested as follows:

Four implantable cardioverter defibrillator (ICD) leads having superior vena cava (SVC) and right ventricular (RV) electrodes were loaded with wet-out agent, two with DSS and two with TDMAC. The ePTFE was 0.012 wall, 0.095 I.D., and 0.120 O.D. The leads had the distal 12 inches covered with ePTFE. The lengths of the two loading zones were as follows:

| loaded length (inches) | nonloaded length (inches) | loaded length (inches) | nonloaded to distal tip (inches) |
|---|---|---|---|
| 2.84 | 4.26 | 1.97 | 0.46 |

The expected volume of solution necessary to fill the pores of the ePTFE over each defibrillation electrode was calculated to be 0.104 cc (104 $\mu$l) for an SVC section and 0.069 cc (69 $\mu$l) for an RV section. An extra 15% was applied to each to ensure that the entire length of each loading zone was coated.

A prototype pipette process was employed to deliver the solution (2% DSS or 10% TDMAC) to the lead. This method uses a 20–200$\mu$l digital, calibrated pipette to withdraw a specific volume (plus a "hold-up" volume) of filtered solution into a custom applicator tip. The tip is an assembly consisting of a sterile, pyrogen free pipette tip that is cut to 0.75 inches long and press fit into a modified 24 gage stainless steel feeding tube. After loading with solution, this assembly is removed from the pipette and immediately used to apply solution to the ePTFE surface at the start of the loading zone. Contacting the ePTFE jacket at the "top" (i.e. 12 o'clock), and holding it at a 45° angle away from the direction of rotation, the tip is moved linearly at a rate such that the capillary wicking of the solution from the tip and onto the lead allows for complete coverage. The lead is clamped at each end and rotated at a constant 60 r.p.m. via a computer-driven dual-stepper motor fixture. The lead is continued to rotate for five minutes during evaporation of the solvent after loading to prevent possible pooling of solution.

Chemicals and Materials Used for Controlled-Quantity Application

DSS: Lot #40416/1 994. (analysis) Mfg. Fluka Chamie AG, Switzerland. Dissolved completely with slight agitation in ~2 minutes in IPA to make 2% solution.
TDMAC: Lot #08914MG. Mfg. Aldrich, prod. number 36,772-9.
IPA: Lot #5194. Mfg. Baxter, catalog number C4307. 99% min., water=0.5% max.
Filter: Lot #3180. Mfg. Gelman, prod. number 4403. Acrodisc® PVDF 0.2 micron,

Gelatin-type Wetting Agent Application: Pressure Methods

In another embodiment, in which the primary agent is gelatin, other proteins (e.g., collagen, albumin) or other similar materials (e.g., agar), the impregnation of the ePTFE may be achieved via immersion/vacuum, perfusion, or pressure processes. Heat and/or vacuum may be used to help dry the lead. Plasticizers such as glycerin may be added to maintain flexibility in the dry state. Wet out "accelerators" (hydrophilic additives such as polysaccharides and polyethylene oxide, or PEO) or therapeutic additives (e.g., antibiotics, antiarrhythmic agents) may be incorporated into the primary agent. While the gelatin may be applied using about 15% gelatin in water, 15% gelatin in 0.9% saline solution may be used as an alternative. When the water is evaporated off, the salt left in the pores with the gelatin accelerates the wetting process and improves conductivity. The membrane may be sterilized using ETO without altering the performance of the wet-out agents.

As a wet-out agent for implantable electrodes, the gelatin does not require crosslinking and can dissolve away immediately. Unlike in grafts, which require the gelatin to remain in place for two weeks to allow for external tissue growth into the outer surface and for the surface of the lumen to become clotted to minimize bleeding, after the gelatin accomplishes its function to wet out the ePTFE it may be washed away from the surface as it dissolves into the blood. Alternatively, gelatin may expand within the pores of the ePTFE and function to prevent tissue adhesion. This may be especially important during the first few weeks of the lead maturation process.

The invention has been described with reference to a preferred embodiment of an implantable endocardial ventricular defibrillation lead. However, the invention may be used for other body implantable leads, such as for subcutaneous or epicardial defibrillation leads, atrial defibrillation leads, leads having sensors, leads for use with pacemakers, neurostimulators, muscle stimulators, and cochlear implants, and stents and vascular grafts. In the case of leads having electrodes covered by a porous material such as ePTFE, the invention provides means for accelerated wetting out of the material to allow current to flow through it. The accelerated wetting is also advantageous in both electrode and nonelectrode applications for the purpose of improving biocompatibility. That is, air is thrombogenic, and quick wetting out removes the thrombogenic air, which is particularly important in blood contacting devices such as stents and vascular grafts.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. A medical device having a body fluid contacting surface for placement within the interior of a patient's body comprising:
    a porous material having open-celled pores comprising a portion of said surface; and
    a sodium sulfosuccinic ester located within said pores in a quantity sufficient to accelerate wetting out of said pores with bodily fluids when said medical device is placed within the interior of said patient.

2. A medical device having a body fluid contacting surface for placement within the interior of a patient's body comprising:
    an electrode;
    a porous material overlaying at least a portion of said electrode and having open-celled pores comprising a portion of said surface; and
    a sodium sulfosuccinic ester located within said pores in a quantity sufficient to accelerate wetting out of said pores with bodily fluids when said medical device is placed within the interior of said patient.

3. The medical device of claim 2 wherein said medical device is an implantable electrical lead for sensing electrical signals from said patient's body or for delivering therapeutic current to said patient, and wherein said medical device further comprises:
    an insulated conductor electrically coupled to said electrode; and
    a lead connector electrically coupled to said insulated conductor.

4. The medical device of claim 2 wherein said sodium sulfosuccinic ester comprises sodium dioctyl sulfosuccinate (DSS).

5. The medical device of claim 4 wherein said DSS is loaded into said pores from a solution of 1% to 10% DSS in isopropanol (IPA).

6. The medical device of claim 5 wherein said DSS is loaded into said pores from a solution of about 2% DSS in IPA.

7. A medical electrical lead for placement within the interior of a patient's body, comprising:
    at least one electrode for sensing electrical signals from said patient's body or for delivering therapeutic current to said patient;
    an insulated conductor electrically coupled to said electrode;
    a lead connector electrically coupled to said insulated conductor;
    a fluoropolymer layer having open-celled pores; and
    a sodium sulfosuccinic ester located within said pores in a quantity sufficient to accelerate wetting out of said pores with bodily fluids when said medical device is placed within the interior of said patient's body.

8. The medical electrical lead of claim 7 wherein said fluoropolymer layer comprises expanded polytetrafluoroethylene (ePTFE).

9. The medical electrical lead of claim 7 wherein said sodium sulfosuccinic ester comprises sodium dioctyl sulfosuccinate (DSS).

10. The medical electrical lead of claim 7 wherein said DSS is loaded into said pores from a solution of 1% to 10% DSS in IPA.

11. The medical electrical lead of claim 10 wherein said DSS is loaded into said pores from a solution of about 2% DSS in IPA.

12. The medical electrical lead of claim 7 wherein said electrode and at least a portion of said insulated conductor are adapted for transvenous implantation.

13. The medical electrical lead of claim 7 and further comprising a hydrogel layer located between said electrode and said fluoropolymer layer.

14. The medical electrical lead of claim 13 wherein said electrode comprises a porous material and wherein said hydrogel layer is mechanically attached to said electrode.

15. The medical electrical lead of claim 13 and further including a chemical bonding agent for chemically bonding said hydrogel layer to said electrode.

16. A method for applying a wetting agent to a porous portion of a medical device comprising the steps of:
    (a) dissolving a sodium sulfosuccinic ester in a solvent to form a sodium sulfosuccinic ester solution;
    (b) applying said sodium sulfosuccinic ester solution to at least a portion of said porous portion of said medical device; and
    (c) evaporating off said solvent.

17. The method of claim 16 wherein said sodium sulfosuccinic ester comprises DSS and wherein said step (a) comprises dissolving a sufficient quantity of DSS in IPA to form a 1% to 10% solution of DSS in IPA.

18. The method of claim 16 wherein said porous portion of said medical device comprises ePTFE and wherein said step (b) comprises applying said sodium sulfosuccinic ester solution to at least a portion of said ePTFE.

19. The method of claim 16 wherein said medical device comprises at least one electrode and wherein said porous portion comprises ePTFE and wherein said step (b) comprises applying said sodium sulfosuccinic ester solution to a portion of said ePTFE which overlies said at least one electrode.

* * * * *